(12) United States Patent
Ko et al.

(10) Patent No.: US 9,550,983 B2
(45) Date of Patent: Jan. 24, 2017

(54) NUCLEIC ACID SEQUENCE SEGMENT FOR ENHANCING PROTEIN EXPRESSION

(71) Applicant: CHINA MEDICAL UNIVERSITY, Taichung (TW)

(72) Inventors: Ying-Chin Ko, Taichung (TW); Chi-Pin Lee, Taichung (TW); Shang-Lun Chiang, Taichung (TW)

(73) Assignee: China Medical University, Taichung (TW)

( * ) Notice: Subject to any disclaimer, the term of this patent is extended or adjusted under 35 U.S.C. 154(b) by 0 days.

(21) Appl. No.: 14/820,836

(22) Filed: Aug. 7, 2015

(65) Prior Publication Data
US 2016/0281069 A1    Sep. 29, 2016

(30) Foreign Application Priority Data

Mar. 27, 2015   (TW) .............................. 104109949 A

(51) Int. Cl.
| | | |
|---|---|---|
| *C12N 15/85* | (2006.01) | |
| *C12N 9/12* | (2006.01) | |
| *G01N 33/573* | (2006.01) | |

(52) U.S. Cl.
CPC ............... *C12N 9/12* (2013.01); *G01N 33/573* (2013.01); *C07K 2319/21* (2013.01); *C07K 2319/43* (2013.01); *C07K 2319/60* (2013.01); *C12Y 207/11* (2013.01); *G01N 2333/912* (2013.01)

(58) Field of Classification Search
None
See application file for complete search history.

(56) References Cited

U.S. PATENT DOCUMENTS 8,916,379 B2 *  12/2014  Ryazanov ............ C12N 9/1205
                                                   435/183

* cited by examiner

*Primary Examiner* — Jim Ketter
(74) *Attorney, Agent, or Firm* — Fishman & Associates, LLC.

(57) ABSTRACT

An isolated or a purified nucleic acid sequence for enhancing expression levels of a protein of interest, in 5' to 3' direction, comprises: a cytomegalovirus (CMV) promoter; an eEF-1 intron repeat (eEF-1 IR); and a regular sequence, which comprises: at least one tag element, a fixable linker sequence, wherein the fixable sequence is TEV sequence; and a multiple cloning site (MCS). By means of the array of the specific promoter and eEF-1 IR, the expression and purity of the recombinant protein could be enhanced; wherein eEF-1 IR can reduce the length of vector and assist RNA polymerase II transcription. Besides, TEV sequence of the fixable linker sequence of the regular sequence can remove a tag on recombinant protein; a specific target can be inserted into the multiple cloning site.

19 Claims, 12 Drawing Sheets

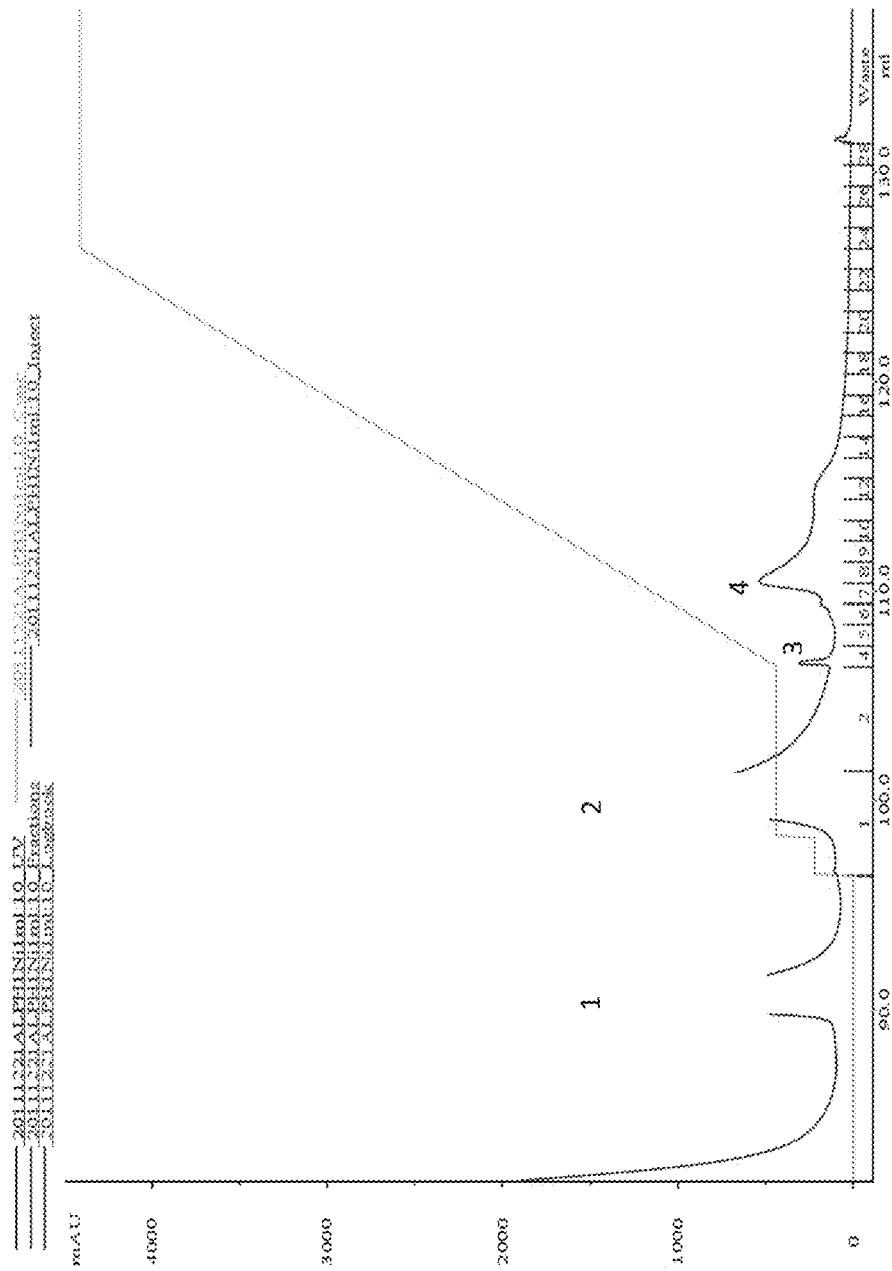

NUCLEIC ACID SEQUENCE SEGMENT FOR ENHANCING PROTEIN EXPRESSION

BACKGROUND OF THE INVENTION

1. Field of the Invention

The present invention relates to a nucleic acid sequence segment, especially to a nucleic acid sequence segment that enhances expression of the recombinant protein segments. The present invention also relates to an expression vector, especially to an expression vector that enhances the expression of recombinant protein. The present invention also relates to a kit, especially to the kit comprising the expression vector and an antibody that can detect the expression of the expression vector.

2. Description of the Prior Arts

Since the physical and chemical properties, folding, structure stability, activity, and protein function can be affected by post-translational modification (PTM), PTM is an extremely important mechanism in biological cells. Phosphorylation is one of the most important post-translational modifications of proteins, and it is involved in a variety of different biological signal pathways; phosphorylation not only refers to a $PO_4$ group binding to a protein or other molecules, but also be defined as an organic phosphate group leading into a molecule, therefore, phosphorylation plays a significant rule in biochemistry field because of its complicated regulation mechanism. Protein phosphorylation occurs at a specific amino acid (the major unit of protein) on which the serine is followed by a threonine Phosphorylation occurring on tyrosine is relatively less, and the location on tyrosine is wider because tyrosine can be purified by antibody easily. Phosphorylation and dephosphorylation respectively require specific enzymes to react, such as protein kinase and phosphatase that can react on particular location on amino acid sequence of the protein. Studies estimate that nearly a third of intracellular proteins are phosphorylated, and nearly half of the protein kinases are related to diseases including cancer. Nowadays, the purification and identification of kinase and phosphatase are still difficult because commercial vectors are unavailable for mass production and recombinant protein kinases purification, and commercial recombinant protein kinases still have low purity and other shortcomings.

The secondary structure of alpha-kinase 1 (ALPK1) is: α-helices overlap in N-terminus, and threonine/serine kinases domain in the C-terminus. There is no sequence homology to conventional protein kinases, and they will mainly phosphorylate at α-helices on substrate of the amino acid. However, the functions of ALPK1 gene is rarely known, and commercially available ALPK1 recombinant protein has disadvantages such as poor expression, only 80% purity, less protein concentration for crystallization, incapability of expression in prokaryotic cells, and mini transfection for eukaryotic cells.

SUMMARY OF THE INVENTION

To overcome the shortcomings of conventional vectors, the objective of the present invention is to provide an expression factor expressing ALPK1 in eukaryotic cells for 90% purification to solve disadvantages of low purity, incapability of expression in prokaryotic cells, and mini transfection into eukaryotic cells.

The present invention provides a purified nucleic acid sequence for enhancing expression levels of a protein of interest, in 5' to 3' direction, comprising: a cytomegalovirus promoter as set forth in SEQ ID NO: 1; an eEF-1 intron repeat (EF-1 IR) as set forth in SEQ ID NO: 2; and a regular sequence, which comprises: at least one tag element, a fixable linker sequence, wherein the fixable sequence is tobacco etch virus identification sequence (TEV sequence) as set forth in SEQ ID NO: 3, and a multiple cloning site (MCS).

According to the present invention, the term "nucleic acid", as used herein, refers to deoxyribonucleotides (DNA), ribonucleotides (RNA), polynucleotides, nucleotides fragment produced by polymerase chain reaction (PCR) or any fragment obtained from ligation, cleaving, endonuclease or exonucleases. Preferably, a protein encoded from nucleic acid is partial or open reading frame (ORF). More preferably, the nucleic acid is single strand or double strand. In one preferred embodiment, the nucleic acid sequence in accordance with the present invention is double DNA sequence.

According to the present invention, the term "promoter", as used herein, refers to a sequence fragment that can be recognized by RNA polymerase, and allows start of gene transcription for the regulation of initiation time and the level of expression. In one preferred embodiment, the promoter in accordance with the present invention is CMV promoter, wherein CMV promoter sequences are well known in the art. In various embodiments of the disclosure, the CMV promoter contains the polynucleotide set forth in SEQ ID NO: 1.

According to the present invention, the term "eEF-1 intron repeat", as used herein, refers to an eukaryotic translation elongation factor 1 alpha 1 (eEF1A1). The first intron of downstream promoter is the eEF1A1 (intron), which can enhance gene expression and protein expression in mammalian cells, mainly 5'un-transcript region (UTR) of eEF1A1 is included in first intron, and the 5' UTR can be recognized and stably bound by RNA polymerase II (RNA Pol II) via the intron to help downstream gene transcription. However, 945 by would increase the length of the vector to limit colony application. Thus, RNA polymerase II bound region is reserved and repeated to decrease the length of vector and enhance transcription within region.

According to the present invention, the term "tag element" as used herein refers to a recombinant polypeptide able to produce small amounts of amino acids. The tag element would not affect the bioactivity of the fusion protein and would not affect polypeptide folding.

Preferably, the at least one tag element is selected from the group consisting of histidine tag (His tag), hemagglutinin tag (HA tag), FLAG™ tag, green fluorescent protein (GFP), turbo GFP, red fluorescent protein (RFP) and glutathione-S-transferase (GST).

According to the present invention, the term "histidine tag," as used herein, refers to a fragment repeat by CATCAC nucleic acid. In one preferred embodiment, the histidine tag in accordance with the present invention is six repeat (6X His tag).

According to the present invention, the term "hemagglutinin tag," as used herein, refers to amino acid sequence YPYDVPDYA (SEQ ID NO.10).

Preferably, the at least one tag element consists of a histidine tag and a hemagglutinin tag preceded by the histidine tag.

Preferably, the at least one tag element consists of a FLAG™ tag and the histidine tag preceded by the FLAG tag™ tag, wherein the FLAG™ tag as used herein, refers to amino acid sequence DYKDDDDK as set forth in SEQ ID NO: 9.

Preferably, the at least one tag element is a green fluorescent protein.

According to the present invention, the term "tobacco etch virus identification sequence (TEV sequence)," as used herein, refers to removal of the tag element of the recombinant fusion protein to recover the prototype of the protein.

According to the present invention, the term "multiple cloning site" refers to location of the downstream of the tag element for inserting specific gene from 5' to 3' direction, wherein the restriction enzyme includes, but is not limited to, Bsp E1, Sal I, Bam HI, Bsm I, Acc I, Xma I, Sma I, Spe I, Sph I, Kpn I, Acc65 I, Ahd I, Cla I, Bsp DI, Not I, Eag I, Fse I, Ngo MI, Nae I, Bse RI, Pme I, Pml I, Aat I, Eco RI, Bse EII, Bst BI, Bsu36 I, Age I, Hind III, Hpa I, Bgl I, Mlu I, Rsr I, Nco I, Nde I, Sca I, Swa I, Sna BI, Xba I, Asis I, Pme I, and Xho I. Preferably, restriction enzyme is Asis I and Pme, wherein Asis I is sticky end, and Pme I is blunt end, thereby increasing ligation efficiency and reducing reverse target gene and vector.

Preferably, the regular sequence further comprises an enhancing element following the multiple cloning site of the regular sequence.

More preferably, the enhancing element consists of an SV40 enhancer and a cytomegalovirus enhancer (CMV enhancer) preceded by the SV 40 enhancer, wherein the SV40 enhancer is as set forth in SEQ ID NO: 4; the CMV enhancer is as set forth in SEQ ID NO: 5.

The present invention also provides an expression vector with said double nucleic acid sequence, wherein the at least one tag element consists of the histidine tag and the hemagglutinin tag preceded by the histidine tag; wherein the at least one enhancing element follows of the regular sequence and comprises the SV40 enhancer and the cytomegalovirus (CMV) enhancer preceded by the SV40 enhancer.

According to the present invention, the term "expression vector," as used herein, refers to a carrier, especially episomal vector; which is designed to reside in vivo and transfect target gene to host cells, and then the expression vectors can express a specific gene and a lot of mRNA. When the expression vector is transfected within the above host cells, target protein can be produced by transcription and translation through particular gene.

Preferably, the expression vector further comprises a selection marker following the enhancer. In one preferred embodiment of the present invention, the selection marker is kanamycin resistance gene as set forth in SEQ ID NO: 6.

According to the present invention, the term "selection marker" as used herein refers to a marker that can be used to identify transfected host or non-transfected cell. In general, the selection marker includes, but is not limited to, resistance for antibiotic, such as neomycin or ampicillin gene; resistance for temperature or resistance for some factor, compound or starving (such as G418). In one preferred embodiment of the present invention, the selection markers such as ampicillin or neomycin resistance are commonly used for preparing agar broth or agar plate.

Preferably, a target gene is inserted into the multiple cloning site of the expression vector by restriction enzyme Asis and pme I.

The present invention also provides an expression vector with said double nucleic acid sequence, wherein the at least one tag element consists of the FLAG™ tag and histidine tag preceded by the FLAG™ tag, and the at least one enhancing element follows the regular sequence and comprises the SV40 enhancer and the cytomegalovirus (CMV) enhancer preceded by the SV40 enhancer.

In a preferred embodiment of the present invention, the methods for transfection include, but are not limited to, calcium phosphate precipitate diethylamino ethyl (diethylaminoethyl, DEAE), exotic virus transfection, liposome mediated lipofection, ballistic transformation, microinjection, transfection, electroporation and other methods as a skilled person knows.

In the preferred embodiment of the present invention, the host cells and cell lines may be a prokaryotic cell or eukaryotic cell, wherein the prokaryotic cell is *Escherichia coli;* wherein the eukaryotic cells include, but are not limited to, human renal epithelial cells HEK293 and variants thereof, hamster ovary cells CHO-S.

The present invention also provides a kit for detecting protein expression, wherein the kit comprises the expression vector and at least one antibody for detecting the protein expressed from the expression vector.

Preferably, the kit further comprises primers for PCR to select nucleic acid sequence for insertion.

In a preferred embodiment of the present invention, the kit of the present invention enables the skilled person to detect the protein expression, the at least one antibody used to detect the protein expression is a first antibody, wherein the first antibody includes, but is not limited to, glutathione S-transferase antibody (GST Ab), anti-histidine antibody, anti-hemagglutinin antibody, anti-FLAG® body or anti-green fluorescent protein antibody. The method used for detecting protein expression includes, but is not limited to, enzyme-linked immunosorbent assay (ELISA) and radio immunoassay (RIA). In more preferable embodiment of the present invention, the kit further comprises a secondary antibody, and the secondary antibody is used to detect the first antibody. The secondary antibody comprises tag protein and includes, but is not limited to, fluorescent-tagged proteins (such as green fluorescent protein or red fluorescent protein), gold particle tag, horseradish peroxidase (HRP) or alkaline phosphatase to detect the amount of protein expression.

Preferably, the kit further comprises multiple restriction enzymes and a ligase, wherein the multiple restriction enzymes are used to cleave a specific site on the multiple cloning site of the expression vector, and the ligase is used to ligate a nucleic acid sequence into the expression vector.

By means of the array of the specific promoter and eEF-1 IR, the expression and purity of the recombinant protein could be enhanced; wherein eEF-1 IR can reduce the length of vector and assist RNA polymerase II transcription. Besides, the advantage of the present invention is that one or more tag elements of the regular sequence can purify target protein; TEV sequence of the fixable linker sequence of the regular sequence can remove a tag on recombinant protein; specific gene can be inserted into the multiple cloning site, and the enhancer of the downstream of the poly A also can enhance protein expression.

BRIEF DESCRIPTION OF THE DRAWINGS

FIG. 6C illustrates the chromatography of the pHH-SV1 expression vector of the present invention by fast protein liquid chromatography (FPLC).

DETAILED DESCRIPTION OF THE PREFERRED EMBODIMENTS

Other objectives, advantages and novel features of the invention will become more apparent from the following detailed description when taken in conjunction with the accompanying drawings.

PREPARATION EXAMPLE 1

Design and Construction of the pHH-SV1 Expression Vector

Figure 1A:
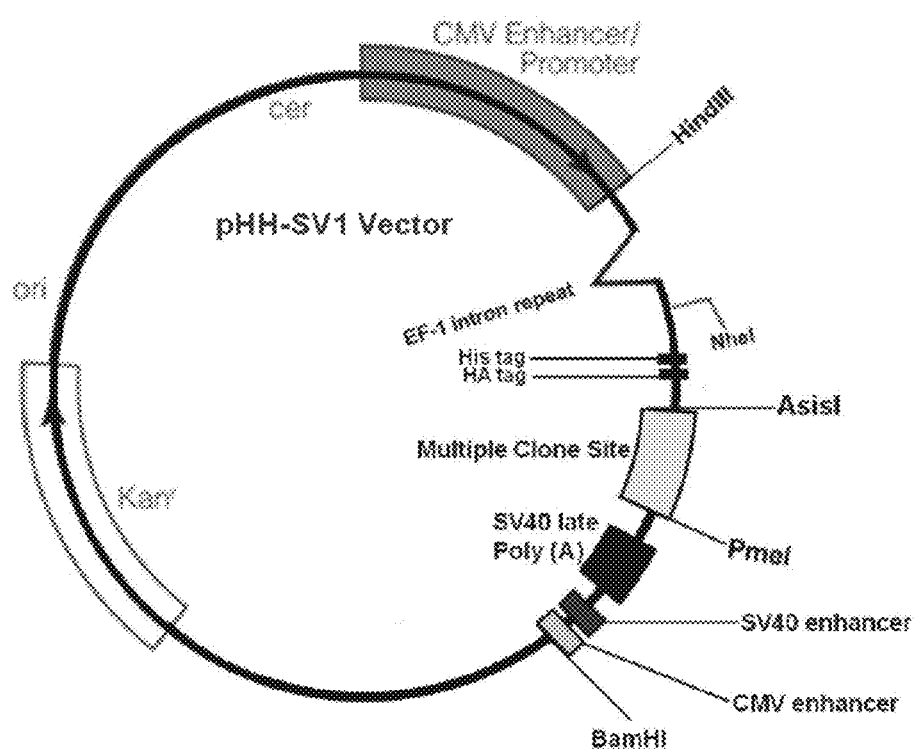
FIG. 1A illustrates a map of the expression vector of pHH-SV1 in accordance with the present invention.
Figure 1B:
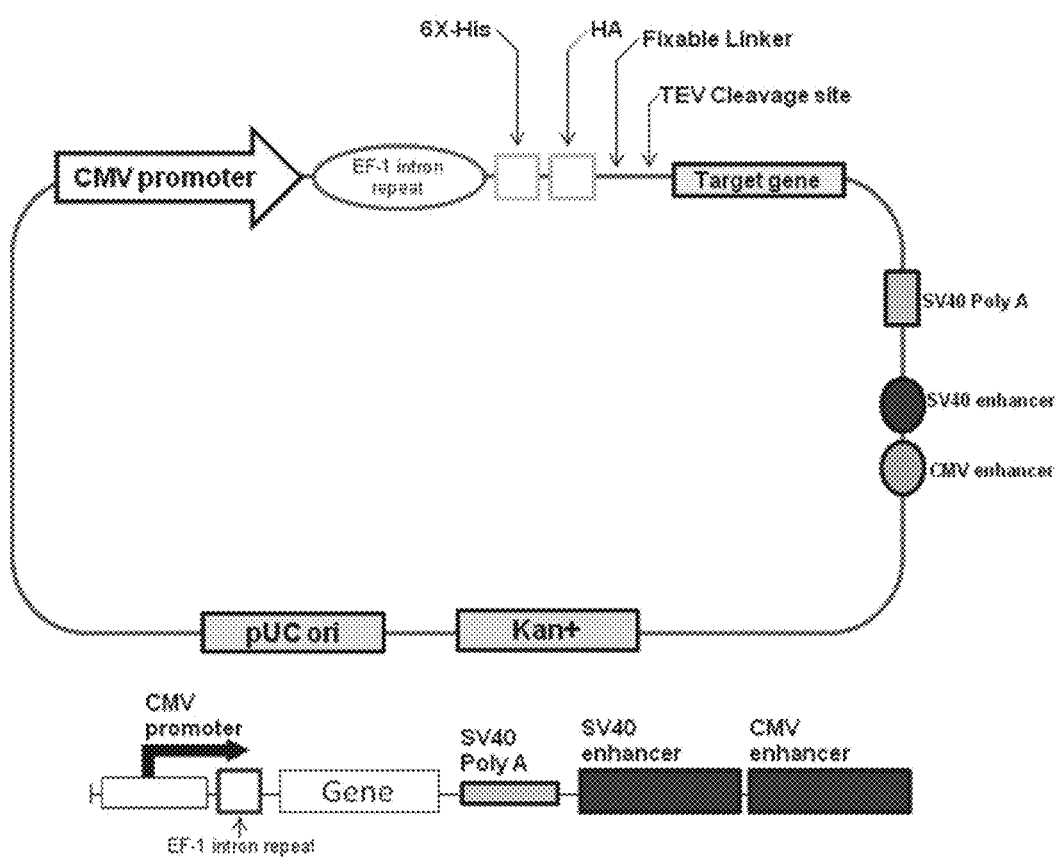
FIG. 1B illustrates a schematic diagram of the expression vector pHH-SV1 in accordance with the present invention.

As shown in FIGS. 1A and 1B, pFN21K vector (purchased from Promega) was used as backbone, 304 by downstream of the CMV promoter (SEQ ID NO: 1) was cleaved by restriction endonucleases Hind III and Nhe I (purchased from Thermo Scientific, catalog numbers: Fermentas FastDigest FD0504 and FD0974, respectively). Subsequently, EF-1 intron repeat having Hind III and Nhe I recognition sites were synthesized by gene synthesis with a forward primer (SEQ ID NO: 7) and a reverse primer (SEQ ID NO: 8) and then ligated into pFN21K vector that had been digested. After cloning, the vector was digested by endonucleases Nhe I and Pme I (purchased from Thermo Scientific, catalog numbers were respectively Fermentas FastDigest FD0974 and FD1344). Then, a regular sequence was ligated to pFN21K, and the regular sequence sequentially comprised 6X-histidine tag®, hemagglutinin (HA) tag, a fixable linker sequence and multiple cloning site (MCS), wherein the fixable linker sequence was tobacco etch virus identification sequence (TEV sequence). An enhancer following the downstream of MCS by PmeI and Bam HI (purchased from Thermo Scientific, catalog numbers: Fermentas FastDigest FD2094 and FD1344, respectively) sequentially comprised SV40 enhance and cytomegalovirus (CMV) enhancer. Finally, a target gene ALPK1 was inserted into MCS, resulting in the pHH-SV1 expression vector.

PREPARATION EXAMPLE 2

Figure 2:
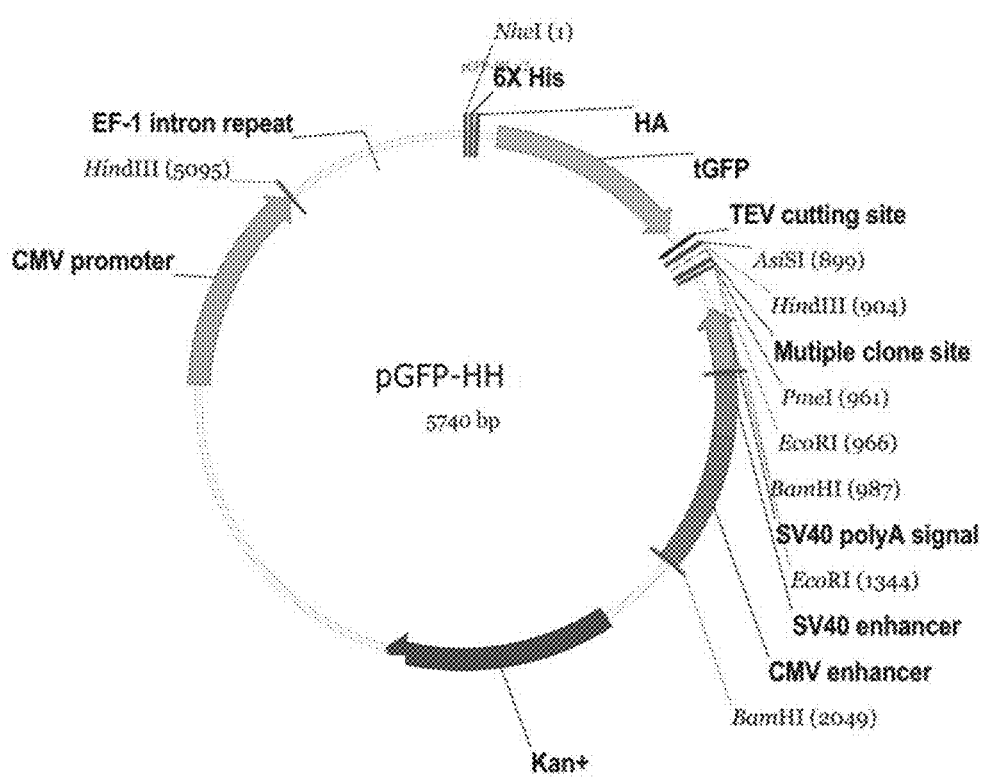
FIG. 2 illustrates a map of the expression vector pGFP-HH in accordance with the present invention.

Design and Construction of the pFH-G2 Expression Vector pFN21K vector was used as backbone, 304 by downstream of the CMV promoter (SEQ ID NO: 1) was cleaved by restriction endonucleases Hind III and Nhe I. Subsequently, EF-1 intron repeat having Hind III and Nhe I recognition sites were synthesized by gene synthesis with a forward primer (SEQ ID NO: 7) and a reverse primer (SEQ ID NO: 8) and then ligated into pFN21K vector that had been digested. After cloning, the vector was digested by endonucleases Nhe I and Pme I. Then, a regular sequence was ligated to pFN21K, and the regular sequence sequentially comprised FLAG™ tag, 6X-histidine tag®, a fixable linker sequence and MCS, wherein the fixable linker sequence was TEV sequence. An enhancer following the downstream of MCS by PmeI and Bam HI sequentially comprised SV40 enhancer and CMV enhancer. Finally, a target gene ALPK1 was inserted into MCS, resulting in the pFH-G2 expression vector (FIG. 2).

PREPARATION EXAMPLE 3

Figure 3:
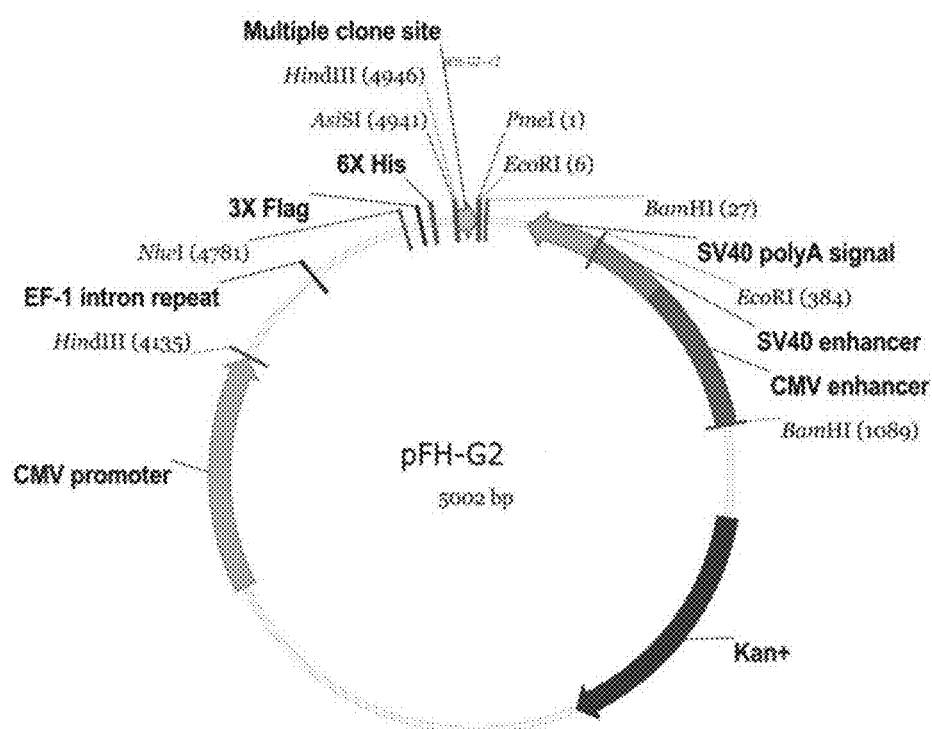
FIG. 3 illustrates a map of the expression vector pFH-G2 in accordance with the present invention.

Design and Construction of the pGFP-HH Expression Vector pFN21K vector was used as backbone, 304 by downstream of the CMV promoter (SEQ ID NO: 1) was cleaved by restriction endonucleases Hind III and Nhe I. Subsequently, EF-1 intron repeat having Hind III and Nhe I recognition sites were synthesized by gene synthesis with a forward primer (SEQ ID NO: 7) and a reverse primer (SEQ ID NO: 8) and then ligated into pFN21K vector that had been digested. After cloning, the vector was digested by endonucleases Nhe I and Pme I. Then, a regular sequence was ligated to pFN21K, and the regular sequence sequentially comprised turboGFP, a fixable linker sequence and MCS, wherein the fixable linker sequence was TEV sequence. An enhancer following the downstream of MCS by PmeI and Bam HI sequentially comprised SV40 enhancer and CMV enhancer. Finally, a target gene ALPK1 was inserted into MCS, resulting in the pGFP-HH expression vector (FIG. 3).

PREPARATION EXAMPLE 4

Purification (1) Mini purification was applied to immunoprecipitation or co-immunoprecipitation. By means of HA tag or FLAG™ tag of fusion protein, target protein could be precipitated via the affinity of antibody and be detected in protein-protein interaction, DNA-protein interaction and kinase assay.

(2) Mega purification was applied to protein crystallization and antibody preparation. The expression vectors pHH-SV1, pFH-G2, and pGFP-HH were respectively expressed in suspension-adapted Human embryonic kidney cells FreeStyleTM293-F (purchased from Life Technologies, catalog number: R790-07) or Hamster Ovary Cells FreeStyleTM-CHO-S (purchased from Life Technologies, catalog number: R800-07). Briefly, 4 μg of vector DNA and 8 μL of Lipofectamine 2000 (purchased from Invitrogen) were used for transient transfection. The transfected HEK 293T cells were cultured under a standard condition (5% $CO_2$ and 37° C.) for 24 hours in erlenmeyer flasks in coordination with orbital shaker prior to harvest. After 48 hours incubation, cells were lysed by microfluidizer and then were centrifuged to obtain a crude protein. The crude protein was purified by immobilized metal affinity chromatography (IMAC) to harvest a target kinase protein.

For example, full length (FL) and N-terminus (Nt) of 6X-His-ALPK1 were respectively inserted into pHH-SV1 expression vectors obtained from preparation example 1, and then the pHH-SV1 expression vectors were respectively expressed in FreeStyle 293-F cells. Cells were lysed using a 27-gauge needle in cell lysis buffer [50 mM HEPES (pH 7.5), 150 mM NaCl, 0.5 mM EDTA, 0.1% Nadeoxycholate, and a Roche complete protease inhibitor cocktail]. The cells were lysed in modified RIPA buffer (50 mM Tris-HCl pH8.0, 150 mM NaCl, 1% NP-40, 1× proteinase inhibitor cocktail mix (purchased from Roche), 1 mM PMSF and 1 mM Na3VO4), and then centrifuged to clarify the lysate. After centrifugation (12,000 g, 20 minutes), the supernatants were respectively supplemented with 20 mM imidazole and loaded on a PD-10 column packed with Ni-Sepharose 6 Fast Flow (purchased from GE Healthcare Biosciences) by gravity and flow. 1 ml Ni-Sepharose 6 Fast Flow was added to supernatants respectively to mix and equilibrate with a 50 mM Tri-HCl buffer, pH 8.0 (containing 150 mM NaCl and 20 mM imidazole). When protein has 6× His-tag, the protein would bind to the Ni-Sepharose 6 Fast Flow carrier. The fractions with carrier were washed in the 30 mM imidazole. The fractions were eluted by 250 mM imidazole, and protein carbohydrate chain modified was analyzed by AcTEV Protease kit (purchased from GE Healthcare Biosciences).

PREPARATION EXAMPLE 5

Substrate Protein Phosphorylation by Target Kinase

To detect phosphorylation, radioactive element γ-32p or γ-33p was calibrated by isotope in commonly in vitro or in vivo study. However, only total amount of phosphated protein can be detected. If a particular phosphorylation site had to be studied, it would take long time to experiment by site-directed mutagenesis.

Therefore, the method of preparation described in Preparation Example 4 was utilized to purify specific protein by native, the steps comprising: reacting total lysates with ATP, adding high salt buffer to quench, purifying by titanium dioxide chromatography to amplify signal of each phosphorylation site, and followed by analysis by tandem mass spectrometer. The sample also can be separated by sodium dodecyl sulfate polyacrylamide gel electrophoresis (SDS-PAGE), and then confirmed total lysate was phospholated by kinase via Pro-Q® Diamond Phosphoprotein Stain (purchased from Life Technologies Inc.)

PREPARATION EXAMPLE 6

Immunoprecipitation

30 μg of total protein from transfected HEK 293 cells was incubated with HA (12CA5, Roche) or Flag (M2, Sigma) antibodies in 50 μL of IP buffer at 4° C. for 4 hours. Protein G mag sepharose (Dynabeads, Invitrogen) were added to the mixture and incubated overnight. The complex was placed on a magnet and washed three times. Proteins eluted from the sepharose beads were subjected to SDS-PAGE and immunoblotting using HA (C29F4, Cell Signaling) or Flag (2EL-1B11, Merck Millipore) antibodies. For sequential reprobing of the same blots, the membranes were stripped and hybridized with another primary antibody. Blots were developed using enhanced chemiluminescence detection kit (Amersham) and protein intensities were quantified using Image J software (version 1.48).

PREPARATION EXAMPLE 7

Liquid Chromatography-Mass Spectrometry (LC-MS)

50 μL of protein solution was thoroughly mixed with 500 μL of acetone following centrifugation at 13,000 rpm for 10 minutes. The protein residues were evaporated to dryness after discarding of the supernatant. Protein residues were redissolved with 25 mM of ammonium bicarbonate aqueous solution and digested with sequence-grade trypsin (Promega) at 37° C. for 16 hours. Subsequently, 2 μL of tryptic peptide solution was injected into the nanoACQUITY UPLC system (Waters, Milford, Mass., USA) containing a desalting column (Symmetry C18, 5 μm, 180 μm×20 mm)

and an analytical column (BEH C18, 1.7 μm, 75 μm×100 mm) and was detected by LTQ Orbitrap Discovery Hybrid fourier transform mass spectrometer (Thermo Fisher Scientific Inc., Bremen, Germany) at a resolution of 30,000 coupled with a nanospray source in a positive ion mode. Individual raw data was processed using Mascot Distiller software (Version 2.2, Matrix Science Inc., Boston, Mass.) and uploaded to the in-house Mascot server for protein identification.

EXAMPLE 1

Protein Expression

Figure 4:
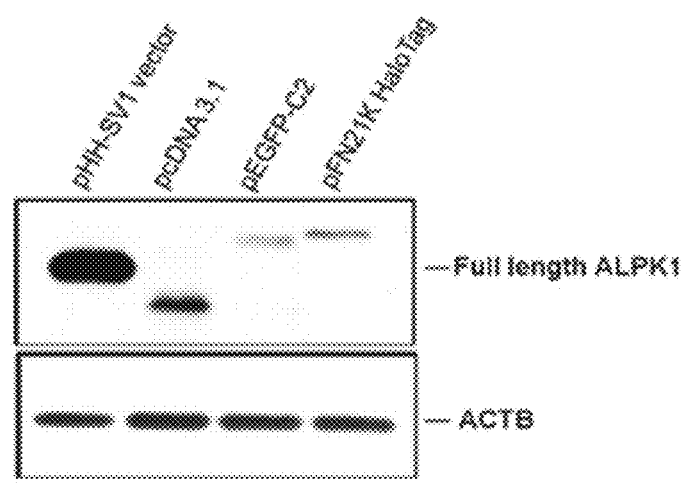
FIG. 4 illustrates the electrophoresis of the protein expression of the expression vector pHH-SV1 in accordance with the present invention and commercially available vectors (pcDNA3.1, pEGFP-C2 and pFN21K HaloTag) by Western blot, wherein column 1 is the pHH-SV1 expression vector of the present invention, column 2 is commercially available vectors pcDNA3.1, column 3 is commercially available vectors pEGFP-C2, and column 4 is commercially available vectors pFN21K HaloTag; ACTB is β-actin as the control group.

The pHH-SV1 expression vector obtained from preparation example 1 was transfected into HEK293T cells, and the protein expression of pHH-SV1 expression vector and commercially available vectors would be detected by Western blotting. As shown in FIG. 4, the ALPK1 protein expression of the pHH-SV1 expression vector in accordance with the present invention was higher than that of the commercially available vectors (pcDNA3.1 purchased from Life Technologies; pEGFP-C2 and pFN21K HaloTag purchased from Promega) in eukaryotic cells. It was said that protein folding and embedding caused by tag of commercially available vectors result in poor protein purification. However, by means of TEV sequence of the fixable sequence cleaving fusion tag, proteins may retain the original state.

Figure 5:
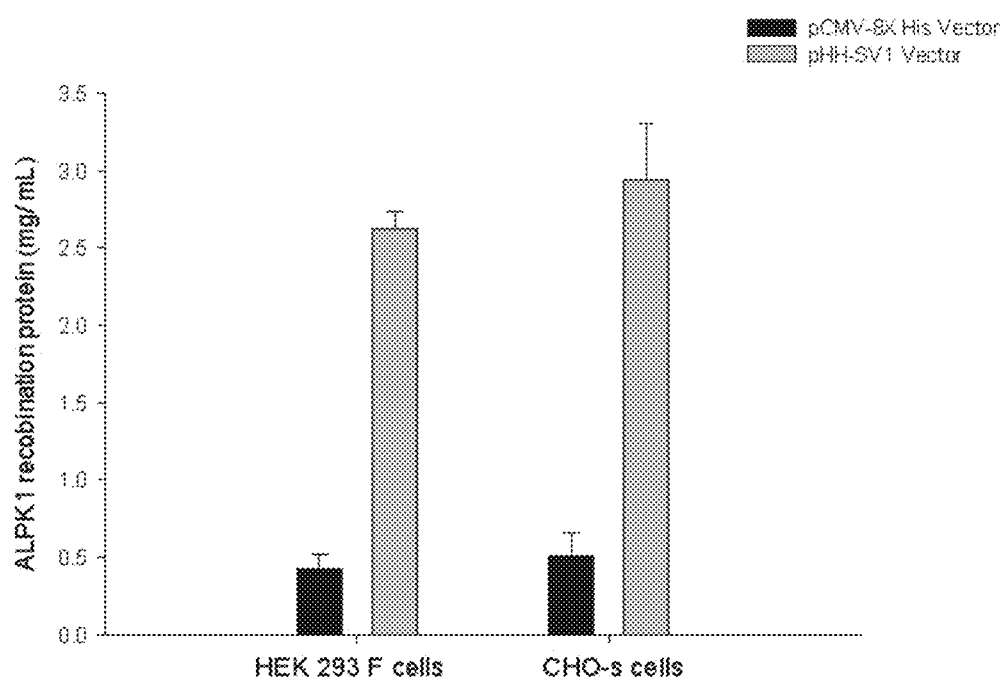
FIG. 5 illustrates protein expression of pHH-SV1 expression vector and pCMV-8X-His vector transfected into HEK293F cell and CHO-S cell respectively.

In addition, when pHH-SV1 expression vector and pCMV-8X-His vector were transfected into HEK239 cells and CHO-S cells respectively, as shown in FIG. 5, the protein expression of the pHH-SV1 expression vector obtained from preparation example 1 was better than pCMV-8X-His vector either in HEK239 cells or CHO-S cells.

EXAMPLE 2

Protein Purity

The pHH-SV1 expression vector obtained from preparation example 1 and pCMV-8X-His vector were purified according to preparation example 4.

Figure 6A:
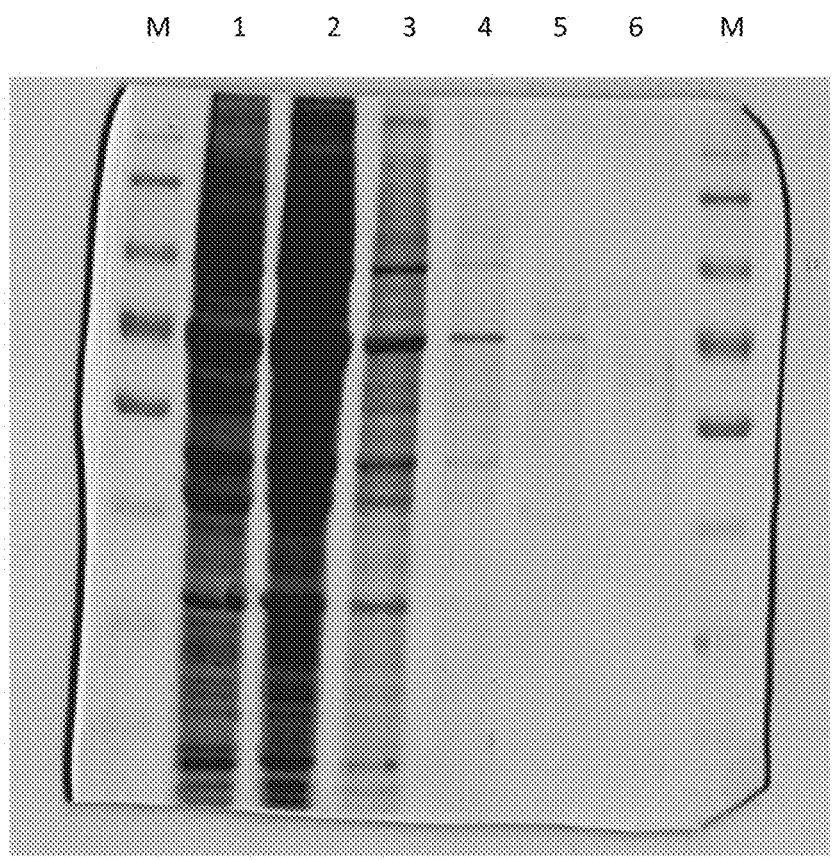
FIG. 6A illustrates the electrophoresis of the pCMV-8X-His vector purification by immobilized metal ion affinity chromatography, wherein M is protein marker (purchased from Fermentas, catalog number: PageRuler™ Prestained Protein Ladder SM0671), column 1 is crude protein, column 2 is flow-through liquid, column 3 is the first washing liquid (wash 1), column 4 is the second washing liquid (wash 2), column 5 is the first eluate (elute 1), and column 6 is the second eluate (elute 2).
Figure 6B:
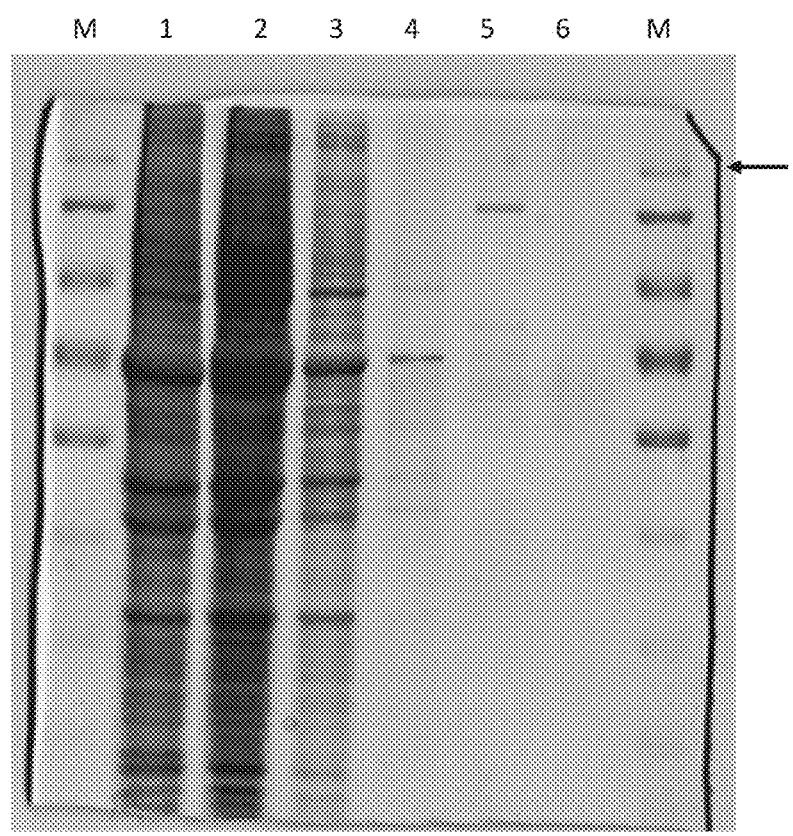
FIG. 6B illustrates the electrophoresis of the pHH-SV1 expression vector purification by immobilized metal ion affinity chromatography, wherein M is protein marker, column 1 is crude protein, column 2 is flow-through liquid, column 3 is the first washing liquid (wash 1), column 4 is the second washing liquid (wash 2), column 5 is the first eluate (elute 1), column 6 is the second eluate (elute 2), and arrow means the molecular weight of ALPK1 protein.

As shown in FIGS. 6A to 6C, in comparison with pCMV-8X-His vector, pHH-SV1 expression vector in accordance with the present invention express a large amount of high purity and active protein. Regarding FIG. 6B, the purity of ALPK1 calculated by software Image J was about 90%.

As shown in FIG. 6C, peaks 1 and 2 were the states of the washing, peak 3 was a first elute, and peak 4 was a second elute; wherein the two peaks 3 and 4 were both the results of eluted ALPK1 amount of protein. Because of most of ALPK1 protein left on the column in peak 3, while increasing the concentration of imidazole, the protein can be released more completely in peak 4 than in peak 3.

EXAMPLE 3

Protein Expression Rate of Co-Transfection pHH-SV1 expression vector obtained from the preparation example 1 and pFH-G2 expression vector obtained from the preparation example 2 were co-transfected into HEK293 cells, wherein the full length of pHH-SV1 expression vector was 142.67 KDa. pFH-G2-MYH9 expression vector expressed myosin IIA, and the full length gene (1 by to 5880 bp) can translate 1960 amino acids (about 220 kDa). pFH-G2-MYH9 Ct expression vector expressed C-terminus truncated protein Myosin IIA (from 4013 by to 5875 bp; total 1863 by translated to 621 a.a.) (about 68.21 kDa). pFH-Rab11a, pFH-PP 1A and vector only (pFH-G2 expression vector) were as a control group, and the protein expressions were detected by Western blotting. An anti-Flag antibody was purchased from Millipro, catalog number: 2EL-1B1. An anti-HA antibody was purchased from Cell signaling, catalog number: C29F4X.

Figure 7:
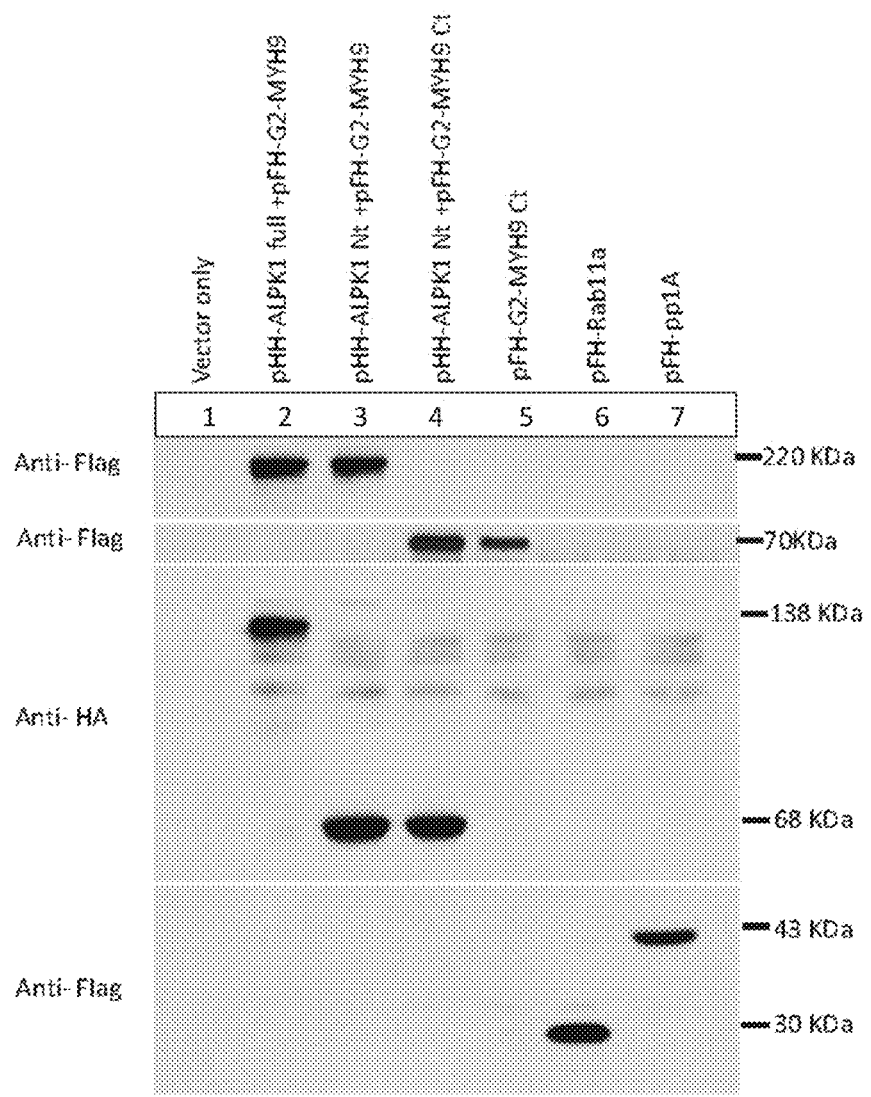
FIG. 7 illustrates the electrophoresis of pHH-SV1 expression vector of the present invention and pFH-G2 expression vector co-transfected to HEK293F cell and detected by Western blot, wherein column 1 is pHH vector (as a control group), column 2 is co-transfected full length of the pHH-SV1 expression vector and pFH-G2-MYH9 expression vector, column 3 is co-transfected N-terminus truncation of pHH-SV1 expression vector and pFH-G2-MYH9 expression vector, column 4 is co-transfected N-terminus truncation of pHH-SV1 expression vector with C-terminus truncation of pFH-G2-MYH9 expression vector, column 5 is the C-terminus truncation of pFH-G2-MYH9 expression vector, column 6 is commercially available pFH-Rab11a vector, column 7 is commercially available pFH-PP1A vector; "anti-Flag" represents the protein expression by anti-FLAG antibody, and "anti-HA" represents the protein expression by anti-anti-HA antibody.

As shown in FIG. 7, since pFH-G2 and pHH-SV1 expression vectors carry different tags respectively, they can be used in protein interaction experiment such as pull-down, immune co-precipitation, and chromatin immunoprecipitation (ChIP). The protein expressions of the pHH-SV1 in accordance with the present invention were consistent (column 2 to column 4).

EXAMPLE 4

The Protein Expression of the Length of ALPK1 Gene

Figure 8:
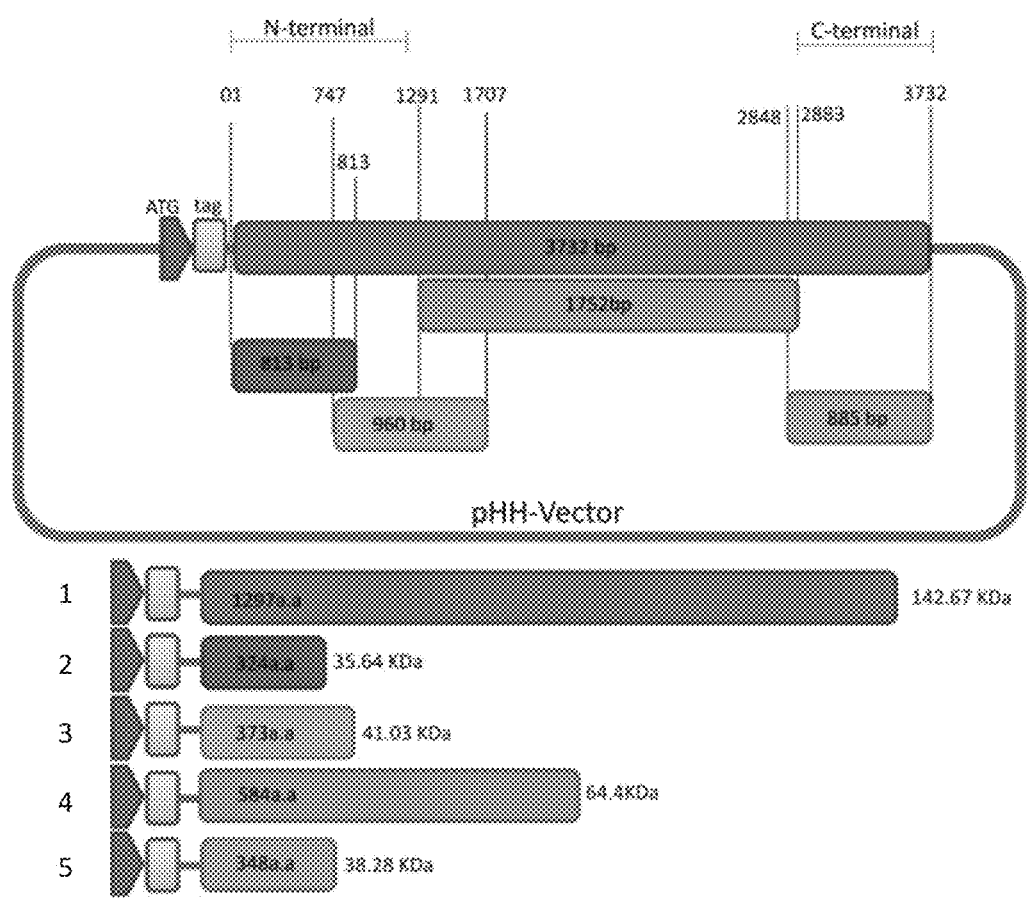
FIG. 8 illustrates a schematic diagram of various deletion forms ALPK1 by PCR, wherein 1 is the full-length protein (1297 amino acids) and the molecular weight of ALPK1 is 142.67 kDa; 2 is 1 to 813 by starting from the N-terminus, the remaining amino acid is 271 a.a and the molecular weight is 35.64 kDa [referred to HA-ALPK1 (Δ1-271)]; 3 is 747 to 1707 by starting from the N-terminus, and the molecular weight is 41.03 kDa [referred HA-ALPK1 (Δ249-569)]; 4 is 1291 to 2883 by starting from the N-terminus, and the molecular weight is 64.4 kDa [referred HA-ALPK1 (Δ431-961)]; 5 is 2848 to 3732 starting from the N-terminus and the molecular weight is 38.28 kDa [referred HA-ALPK1 (Δ950-1244)].
Figure 9:
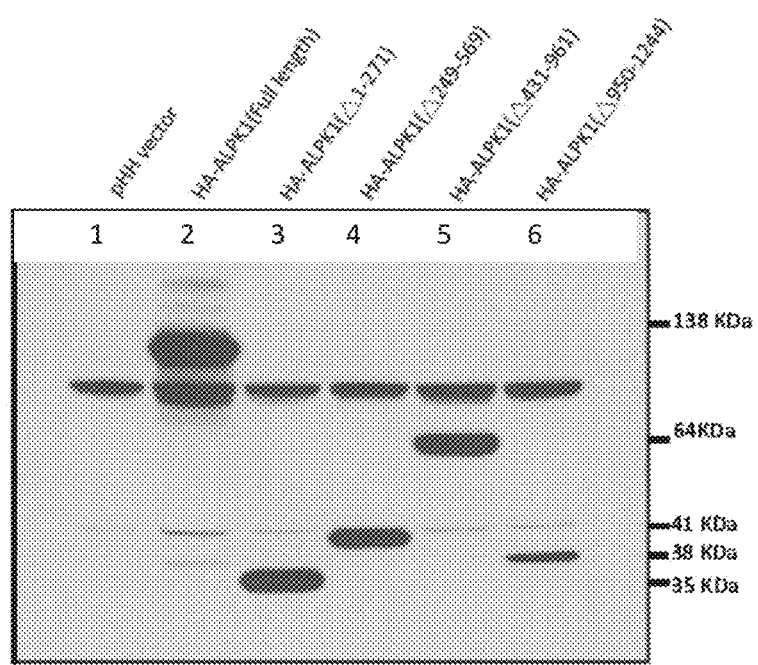
FIG. 9 illustrates the electrophoresis of various deletion forms of ALPK1 inserted into pHH-SV1 expression vector of the invention, and then transfected into HEK293T cells by Western blot, wherein column 1 is pHH vector (as a control); column 2 is full length ALPK1 protein and the molecular weight is 142.67 kDa, column 3 is HA-ALPK1 (Δ1-271) and the molecular weight is 35.64 kDa, column 4 is HA-ALPK1 (Δ249-569) and the molecular weight is 41.03 kDa, column 5 is HA-ALPK1 (Δ431-961) and the molecular weight is 64.4 kDa, and column 6 is HA-ALPK1 (Δ950-1244) and the molecular weight is 38.28 kDa.

As shown in FIGS. 8 and 9, ALPK1 gene was designed by PCR to obtain various deletion forms, the deletion forms of ALPK1 gene were inserted to the pHH-SV1 expression vector in accordance with the present invention and then transfected to HEK293T cells, and the protein expression of the deletion forms of ALPK1 gene was analyzed by Western blotting; wherein the various deletion forms of ALPK1 gene all can express ALPK1 protein.

What is claimed is:

1. An isolated or a purified nucleic acid sequence for enhancing expression levels of a protein of interest, in 5' to 3' direction, comprising:
   a cytomegalovirus (CMV) promoter as set forth in SEQ ID NO: 1;
   an eEF-1 intron repeat (eEF-1 IR) as set forth in SEQ ID NO: 2; and
   a regular sequence comprising:
      at least one tag element,
      a fixable linker sequence, wherein the fixable linker sequence is tobacco etch virus identification sequence (TEV sequence) as set forth in SEQ ID NO: 3; and
      a multiple cloning site (MCS).

2. The nucleic acid sequence as claimed in claim 1, wherein the at least one tag element is selected from the group consisting of histidine tag (His tag), hemagglutinin tag (HA tag), FLAG tag, green fluorescent protein (GFP), turbo GFP, red fluorescent protein (RFP) and glutathione-S-transferase (GST).

3. The nucleic acid sequence as claimed in claim 1, wherein the at least one tag element consists of a histidine tag and a hemagglutinin tag preceded by the histidine tag.

4. The nucleic acid sequence as claimed in claim 1, wherein the at least one tag element consists of a FLAG tag and a histidine tag preceded by a FLAG tag.

5. The nucleic acid sequence as claimed in claim 1, wherein the at least one tag element is a green fluorescent protein.

6. The nucleic acid sequence as claimed in claim 1, wherein the regular sequence further comprises an enhancing element following the multiple cloning site of the regular sequence.

7. The nucleic acid sequence as claimed in claim 6, wherein the enhancing element consists of an SV40 enhancer and a cytomegalovirus (CMV) enhancer preceded by the SV 40 enhancer.

8. An expression vector comprising:
   the nucleic acid sequence as claimed in claim 1, comprising:
      two tag elements consisting of the histidine tag and the hemagglutinin tag preceded by the histidine tag; and,
      at least one enhancing element following the regular sequence, wherein the at least one enhancing element comprises an SV40 enhancer and a cytomegalovirus (CMV) enhancer preceded by the SV40 enhancer.

9. The expression vector as claimed in claim 8, wherein the expression vector further comprises a selection antibiotic following the enhancer, wherein the selection antibiotic is selected from the group consisting of ampicillin, kanamycin, chloramphenicol, tetracyclin, hygromycin, neomycin or methotrexate.

10. The expression vector as claimed in claim 8, wherein a target gene ALPK1 is inserted into the multiple cloning site by restriction enzyme Asis I and pmer I.

11. An expression vector comprising:
   the nucleic acid sequence as claimed in claim 1 comprising:
      two tag elements consisting of a FLAG tag and a histidine tag preceded by the FLAG tag; and
      at least one enhancing element following the regular sequence, wherein the at least one enhancing element comprises an SV40 enhancer and a cytomegalovirus (CMV) enhancer preceded by the SV40 enhancer.

12. The expression vector as claimed in claim 11, wherein the expression vector further comprises a selection antibiotic following the enhancer, wherein the selection antibiotic is selected from the group consisting of ampicillin, kanamycin, chloramphenicol, tetracyclin, hygromycin, neomycin or methotrexate.

13. The expression vector as claimed in claim 11, wherein a target gene ALPK1 is inserted into the multiple cloning site by restriction enzyme Asis I and pmer I.

14. An expression vector comprising:
   the nucleic acid sequence as claimed in claim 1;
   the tag element being green fluorescent protein; and,
   at least one enhancing element following the regular sequence, wherein the at least one enhancing element comprises an SV40 enhancer and a cytomegalovirus (CMV) enhancer preceded by the SV40 enhancer.

15. The expression vector as claimed in claim 14, wherein the expression vector further comprises a selection antibiotic following the enhancer, and the selection antibiotic is selected from the group consisting of ampicillin, kanamycin, chloramphenicol, tetracyclin, hygromycin, neomycin or methotrexate.

16. The expression vector as claimed in claim 14, wherein a target gene ALPK1 is inserted into the multiple cloning site by restriction enzyme Asis I and pmer I.

17. A kit for detecting protein expression comprising:
   the vector of claim 8,
   at least one antibody for detecting the protein expression from the vector, wherein the antibody is selected from the group consisting of anti-histidine tag antibody, anti-hemagglutinin tag antibody, and combination thereof.

18. A kit for detecting protein expression comprising:
   the vector of claim 11,
   at least one antibody for detecting the protein expression from the vector, wherein the antibody is selected from the group consisting of anti-histidine tag antibody, anti-FLAG tag antibody, and combination thereof.

19. A kit for detecting protein expression comprising:
   the vector of claim 14,
   an antibody for detecting the protein expression from the vector, wherein the antibody is anti-green fluorescent protein antibody.

\* \* \* \* \*

SEQUENCE LISTING

```
<160> NUMBER OF SEQ ID NOS: 10

<210> SEQ ID NO 1
<211> LENGTH: 742
<212> TYPE: DNA
<213> ORGANISM: Unknown
<220> FEATURE:
<223> OTHER INFORMATION: cytomegalovirus

<400> SEQUENCE: 1
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
```

```
gtcattagtt catagcccat atatggagtt ccgcgttaca taacttacgg taaatggccc    240
gcctggctga ccgcccaacg accccgccc attgacgtca ataatgacgt atgttcccat     300
agtaacgcca atagggactt tccattgacg tcaatgggtg gagtatttac ggtaaactgc    360
ccacttggca gtacatcaag tgtatcatat gccaagtccg cccctattg acgtcaatga     420 cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaataaccc    660
cgccccgttg acgcaaatgg gcggtaggcg tgtacggtgg gaggtctata taagcagagc    720
tggtttagtg aaccgtcaga tc                                             742

<210> SEQ ID NO 2
<211> LENGTH: 652
<212> TYPE: DNA
<213> ORGANISM: Unknown
<220> FEATURE:
<223> OTHER INFORMATION: eukaryotic translation elongation factor 1

<400> SEQUENCE: 2
aagcttgtaa gtgccgtgtg tggttcccgc gggcctggcc tctttacggg ttatggccct    60
tgcgtgcctt gaattacttc cacctggctg cagtacgtga ttcttgatcc cgagcttcgg    120
gttggaagtg ggtgggagag ttcgaggcct tgcgcttaag gagccccttc gcctcgtgct    180
tgagttgagg cctggcctgg gcgctggggc cgccgcgtgc gaatctggtg gcaccttcgc    240
gcctgtctcg ctgctttcga taagtctcta gccatttaaa attttgatg acctgctgcg    300 acgcttttt tctggcaaga tagtcttgta aatgcgggcc aagatctgca cactggtatt    360
tcggtttttg gggccgcggg cggcgacggg gcccgtgcgt cccagcgcac atgttcggcg    420
aggcggggcc tgcgagcgcg gccaccgaga tcggacgggg ggtagtctca agctggccgg    480
cctgctctgg tgcctggcct cgcgccgccg tgtatcgccc cgccctgggc ggcaaggctg    540
gcccggtcgg caccagttgc gtgagcggaa agatggccgc ttcccggccc tgctgcaggg    600
ccgcttcccg gccctgctgc agggccgctt cccggccctg ctgcaggcta gc            652

<210> SEQ ID NO 3
<211> LENGTH: 21
<212> TYPE: DNA
<213> ORGANISM: Unknown
<220> FEATURE:
<223> OTHER INFORMATION: Tobacco etch virus

<400> SEQUENCE: 3
gaggatctgt actttcagag c                                              21

<210> SEQ ID NO 4
<211> LENGTH: 216
<212> TYPE: DNA
<213> ORGANISM: Unknown
<220> FEATURE:
<223> OTHER INFORMATION: Simian virus 40

<400> SEQUENCE: 4
tgtgtcagtt agggtgtgga aagtccccag gctccccagc aggcagaagt atgcaaagca    60
tgcatctcaa ttagtcagca accaggtgtg gaaagtcccc aggctcccca gcaggcagaa    120
gtatgcaaag catgcatctc aattagtcag caaccatagt cccgccccta actccgccca    180
```

```
tcccgcccct aactccgccc agttccgccc attctc                                216
```

<210> SEQ ID NO 5
<211> LENGTH: 479
<212> TYPE: DNA
<213> ORGANISM: Unknown
<220> FEATURE:
<223> OTHER INFORMATION: cytomegalovirus

<400> SEQUENCE: 5

```
cgttacataa cttacggtaa atggcccgcc tggctgaccg cccaacgacc cccgcccatt         60
gacgtcaata atgacgtatg ttcccatagt aacgccaata gggactttcc attgacgtca       120
atgggtggag tatttacggt aaactgccca cttggcagta catcaagtgt atcatatgcc       180
aagtacgccc cctattgacg tcaatgacgg taaatggccc gcctggcatt atgcccagta       240
catgacctta tgggactttc ctacttggca gtacatctac gtattagtca tcgctattac       300
catggtgatg cggttttggc agtacatcaa tgggcgtgga tagcggtttg actcacgggg       360
atttccaagt ctccacccca ttgacgtcaa tgggagtttg ttttggcacc aaaatcaacg       420
ggactttcca aaatgtcgta acaactccgc cccattgacg caaatgggcg gtaggcgtg       479
```

<210> SEQ ID NO 6
<211> LENGTH: 795
<212> TYPE: DNA
<213> ORGANISM: Unknown
<220> FEATURE:
<223> OTHER INFORMATION: Streptomyces kanamyceticus

<400> SEQUENCE: 6

```
atgcttgaac aagatggatt gcacgcaggt tctccggccg cttgggtgga gaggctattc         60
ggctatgact gggcacaaca gacaatcggc tgctctgatg ccgccgtgtt ccggctgtca       120
gcgcaggggc gcccggttct ttttgtcaag accgacctgt ccggtgccct gaatgaactg       180
caggacgagg cagcgcggct atcgtggctg gccacgacgg gcgttccttg cgcagctgtg       240
ctcgacgttg tcactgaagc gggaagggac tggctgctat tgggcgaagt gccggggcag       300
gatctcctgt catctcacct tgctcctgcc gagaaagtat ccatcatggc tgatgcaatg       360
cggcggctgc atacgcttga tccggctacc tgcccattcg accaccaagc gaaacatcgc       420
atcgagcgag cacgcactcg gatggaagcc ggtcttgtcg atcaggatga tctggacgaa       480
gagcatcagg ggctcgcgcc agccgaactg ttcgccaggc tcaaggcgcg tatgccggat       540
ggtgaggatc tcgtcgtgac tcatggcgat gcctgcttgc cgaatatcat ggtggaaaat       600
ggccgctttt ctggattcat cgactgtggc cggctgggtg tggcggaccg ctatcaggac       660
atagcgttgg ctacccgtga tattgctgaa gagcttggcg gcgaatgggc tgaccgcttc       720
ctcgtgcttt acggtatcgc cgctcccgat tcgcagcgca tcgccttcta tcgccttctt       780
gacgagttct tctga                                                        795
```

<210> SEQ ID NO 7
<211> LENGTH: 20
<212> TYPE: DNA
<213> ORGANISM: Artificial Sequence
<220> FEATURE:
<223> OTHER INFORMATION: For synthesizing EF-1 intron repeat

<400> SEQUENCE: 7

```
gaaagatggc cgcttcccgg                                                    20
```

```
<210> SEQ ID NO 8
<211> LENGTH: 22
<212> TYPE: DNA
<213> ORGANISM: Artificial Sequence
<220> FEATURE:
<223> OTHER INFORMATION: For synthesizing EF-1 intron repeat

<400> SEQUENCE: 8
cctgagtgct tgcggcagcg tg                                              22

<210> SEQ ID NO 9
<211> LENGTH: 8
<212> TYPE: PRT
<213> ORGANISM: Artificial Sequence
<220> FEATURE:
<223> OTHER INFORMATION: synthesized

<400> SEQUENCE: 9

Asp Tyr Lys Asp Asp Asp Asp Lys
1               5

<210> SEQ ID NO 10
<211> LENGTH: 9
<212> TYPE: PRT
<213> ORGANISM: Artificial Sequence
<220> FEATURE:
<223> OTHER INFORMATION: synethesized

<400> SEQUENCE: 10

Tyr Pro Tyr Asp Val Pro Asp Tyr Ala
1               5
```